United States Patent [19]

Papaphilippou

[11] Patent Number: 4,781,916

[45] Date of Patent: Nov. 1, 1988

[54] COSMETIC PREPARATION

[75] Inventor: Alexander P. Papaphilippou, Amanzimtoti, South Africa

[73] Assignee: Karl Heinrich Pegel

[21] Appl. No.: 85,237

[22] Filed: Aug. 12, 1987

Related U.S. Application Data

[63] Continuation of Ser. No. 734,374, May 15, 1985, abandoned.

[30] Foreign Application Priority Data

May 24, 1984 [ZA] South Africa .................... 84/3939

[51] Int. Cl.$^4$ .............................................. A61K 7/047
[52] U.S. Cl. ............................. 424/61; 252/DIG. 8; 252/162
[58] Field of Search ............ 424/61; 252/162, DIG. 8

[56] References Cited

U.S. PATENT DOCUMENTS

| | | | |
|---|---|---|---|
| 1,516,064 | 11/1924 | Schmidt | 252/DIG. 8 |
| 2,765,257 | 10/1956 | Blackburn | 424/61 |
| 3,150,048 | 9/1964 | Hollub et al. | 424/61 |
| 3,482,923 | 12/1969 | Boosen et al. | 8/568 |
| 3,565,571 | 2/1971 | Reese et al. | 8/573 |
| 3,624,221 | 11/1971 | Lange et al. | 514/785 |
| 3,833,720 | 9/1974 | Crotty et al. | 424/47 |
| 4,052,513 | 10/1977 | Kaplan | 514/938 |
| 4,239,641 | 12/1980 | Perner et al. | 252/162 |

FOREIGN PATENT DOCUMENTS

| | | | |
|---|---|---|---|
| 1288749 | 2/1969 | Fed. Rep. of Germany | 424/70 |
| 1467891 | 6/1969 | Fed. Rep. of Germany | 424/61 |
| 1492194 | 12/1969 | Fed. Rep. of Germany | 424/70 |
| 2192798 | 2/1974 | France | 424/47 |

OTHER PUBLICATIONS

Chemical Abstracts, 1979, vol. 90, pp. 61078m.
Janistyn, Handbuch der Kosmetik und Riechstoffe, 2nd ed., 1973, pp. 935–937.
Janistyn, (I) Reichstoffe Seifen Kosmetika, Band II, 1950, pp. 421.
Hayashi et al, Chem. Abs., 1979, vol. 90, pp. 142085p.
Matsumoto et al, Chem. Abs., 1977, vol. 86, p. 95879f.
Rinaldi et al, Chem. Abs., 1975, vol. 81, p. 82256.
Asada et al, Chem. Abs., 1974, vol. 80, 19403g.
Shimizu, Chem. Abs., 1980, vol. 92, p. 82250t.
Crotty, Chem. Abs., 1975, vol. 81, p. 82258z.
Pat. Abs. Japan, vol. 8, No. 222, 10/9/84, JP-A-59106411.

*Primary Examiner*—Dale R. Ore
*Attorney, Agent, or Firm*—Pennie & Edmonds

[57] ABSTRACT

The invention relates to a cosmetic preparation for the removal of nail varnish in particular but which also has skin cleansing properties, the preparation containing a diester of a diol or a dioic acid and having between 4 and 10 carbon atoms per molecule.

15 Claims, No Drawings

COSMETIC PREPARATION

This is a continuation of application Ser. No. 734,374, filed May 15, 1985, now abandoned.

FIELD OF THE INVENTION

This invention relates to a cosmetic preparation which is mainly useful for removing nail varnish, stregthening the nail structure and improving cuticle texture. It is also useful as a skin cleanser and conditioner for both beauty care and industrial purposes.

BACKGROUND OF THE INVENTION

Conventional nail polish removers, such as acetone, cause dehydration and dewaxing. They remove natural lipids from the nails and surrounding cuticles.

Another problem with conventional nail polish removers, such as acetone, is that they evaporate and spill easily. This disadvantage as well as other disadvantages referred to above have been alleviated to an extent by providing a gel containing acetone with other additives such as colourants, vitamins, proteins and the like. However, the main disadvantage persists and it is an object of the present invention to provide a composition which not only removes nail varnish effectively, but which also acts as a moisturiser and tissue care agent.

THE INVENTION

According to the invention a cosmetic preparation includes one or more esters of dicarboxylic acids and preferably diesters of dicarboxylic acids of the formula $$R^1OOC-(L)-COOR^2$$

and one or more esters of diols and preferably diesters of diols of the formula $$R^1-CO-O-(M)-O-CO-R^2$$

in which $R^1$ and $R^2$ may be the same or different and each may have from 1 to 7 carbon atoms when combined with L, and from 1 to 5 carbon atoms when combined with M. L consists of 0 to 4 skeletal bridge carbon atoms which may be substituted, fully saturated (one or two double or triple bonds), and if substituted may carry no more extra carbon containing substituents than to provide a total of 10 carbon atoms for the entire diester molecule. M consists of 2 to 6 skeletal bridge carbon atoms which may be substituted or cyclised, fully saturated, or unsaturated (one or two double or triple bonds), and if substituted may carry no more carbon containing substituents than to provide a total of 10 carbon atoms for the entire diester molecule.

In addition it is preferred that no more than two functional groups (for example OH, OR, COOR, where R has the meaning as above) may be present and ether oxygens may link two or more of the carbon atoms in L, M or R.

According further to the invention the preferred diesters are derived from simple dicarboxylic acids or diols. The preferred dicarboxylic acid esters are the diethyl esters of oxalic-, malonic-, succinic-, glutaric-, and adipic acids, and their simple derivatives. The preferred diol esters are the diacetates of 1,2-ethanediol, 1,2- and 1,3-propanediol, various positional and structural isomers of butanediol, pentanediol, and hexanediol including cyclopentane- and cyclohexane diols as well as the corresponding diesters of dioxyethylene- and trioxyethylene glycols, and their simple derivatives.

The diester or diester mixture responsible for dissolving the film forming ingredients in nail varnish make-up preparations may be contained in a solid or semi solid matrix as an oil in water (O/W) or water in soil (W/O) emulsion. The solid or semi solid matrix, besides being a good vehicle for the solvent or solvent blend, provides the lipid or fatty "nourishing" material which counteracts the lipid stripping effect of the solvent(s) thereby avoiding any tissue hardening and damage which provides access to attack by micro-organisms.

The diesters are not water soluble and can therefore not act as dehydrating agents. On the contrary, the water content of the composition provides a moisturising effect.

The compositions of the invention may also contain one or more lipids such as lanolin, various vegetable and animal oils and fats, sterols; moisturisers such as glycerol, monoalkyl ethers of ethylene and propylene glycols and the like.

In addition the matrix may contain surfactants (non-ionic, anionic, cationic) to provide not only emulsifying properties, but also water solubility of the emulsion on removal.

The preferred lipids of the invention are lanolin, plant oils and fats, paraffin (hard, soft, or liquid), cholesterol, sitosterol and the like.

The preferred emulsifiers of the invention are emulsifying wax (B.P.), or (U.S.P.), glycerin monostearate (self emulsifying), Span 60 (10-80), Tween 60 (10-80), polyoxyethylene sterols as primary emulsifiers, and sodium lauryl sulphates as secondary emulsifiers or equivalent emusifiers according to the state of the art.

The preferred moisturisers are monomethyl ethers of ethylene—and propylene glycol. Equivalent moisturisers according to the state of art may be substituted.

Any acceptable preservative can be used, such as butylated hydroxy anisole (BHA), butylated hydroxytoluene (BHT) and the like.

The nail varnish cleansing and tissue conditioning cosmetic may be applied to the nail surface and surrounding tissue with gentle massage for a period of up to two minutes before the treated area is either wiped or rinsed with water; the process can be repeated.

Use of the compositions of the invention not only prevents hardening, embrittlement and cracking of the nails, cuticles and surrounding skin, but ensures that these tissues remain supple and well nourished and remain free from microbial attack and physical damage due to tissue degradation.

The cosmetic products of this invention also act as cleansing agents for the removal of foreign matter such as make-up, (with the possible exception of eye make-up), industrial grime of varied origin, paint, and dirt in general. By replenishing essential moisture and lipid nutrients to skin tissue, these products prevent skin hardening and thus premature aging.

The products of the invention not only achieve the "cleansing" process in an effective and agreeable manner, but at the same time prevent aggressive stripping of moisture and lipids and provide concomitant nail and skin care. Indeed experience has shown that there is a noticeable prevention in nail embrittlement and improvement in texture of the nails and surrounding tissue. An added bonus is the safety aspect since the viscous nature of the products, which ranges from a thick oil to a soft creamy consistency, are spill resistant, and the "solvents" do not evaporate rapidly.

EXAMPLE 1

| A | Diethyl succinate | 46.3% |
|---|---|---|
|   | Lanolin (anhydrous) | 4.6% |
|   | Hard paraffin | 4.6% |
|   | Emulsifying wax (B.P.) | 4.6% |
|   | Glycerin monostearate (self-emulsifying) | 16.7% |
| B | Propylene glycol monomethyl ether | 13.9% |
|   | Water | 9.3% |

Heat A and B separately to 70°–75° C. Add B to A slowly, and cool gradually with agitation; add preservative, colourant and perfume, as required, at 50° C.

NOTES (a) The diester solvent may be replaced with any one or mixtures of the preferred solvents specified above ranging from 10 to 90% but preferably 40 to 60%.
(b) Anhydrous lanolin may be substituted by water soluble or liquid lanolin, hydrogenated wool fat, various sterols, and the like up to 20% but preferably between 3 and 10%.
(c) Hard paraffin may be substituted by liquid or soft paraffin, or vegetable or animal oil and fats ranging between 1 and 20% but preferably between 2 and 10%.
(d) The emulsifier may consist of an appropriate combination of non-ionic, anionic or cationic surfactants to achieve the desired hydrophilic to lipophilic balance between 4 to 12 but preferably between 6 and 8.
(e) The propylene glycol monomethyl ether may be replaced by glycerol and glycols and their derivatives with humectant properties in the range of 5 to 15%.
(f) The water content is adjusted accordingly to 100%. Preservative addition is optional but if more than 10% water is included a preservative may be added up to 0.5%.

EXAMPLE 2

| A | 1,2-Ethanediol diacetate | 40% |
|---|---|---|
|   | Lanolin (anhydrous) | 4% |
|   | Hard paraffin | 4% |
|   | Span 60 | 8% |
|   | General E-5 | 4% |
| B | Propylene glycol monomethyl ether | 10% |
|   | Water | 30% |
|   | Preservative | q.s. |
|   | Perfume | q.s. |

The method of preparation is as follows: Heat A and B separately to 70°–75° C. and slowly add B to the oily phase with stirring. Add preservatives, colourants and perfumes at 50° C.

EXAMPLE 3

| A | 1,2-Propanediol diacetate | 50% |
|---|---|---|
|   | Lanolin (anhydrous) | 4% |
|   | Hard paraffin | 4% |
|   | Span 60 | 8% |
|   | General E-5 | 4% |
| B | Water | 30% |
|   | Preservatives | q.s. |
|   | Perfume | q.s. |

EXAMPLE 4

| Diethyl malonate | 40–60% |
|---|---|
| Emulsifying wax (B.P.) | 5–15% |
| Hard paraffin | 2–5% |
| Glyceryl monostearate (self-emulsifying) | 5–14% |
| Preservative | 0.1% |
| Water | to 100% |

EXAMPLE 5

| Diethyl oxalate | 40–47% |
|---|---|
| Lanolin (anhydrous) | 5–10% |
| Span 60 | 6–8% |
| Tween 60 | 1–2% |
| Sodium lauryl sulphate | 1–2% |
| Preservative | 0.1% |
| Water | to 100% |

EXAMPLE 6

| Diethyl succinate | 40–45% |
|---|---|
| Lanolin (anhydrous) | 10–13% |
| Hard paraffin | 4–5% |
| Span 60 | 6–7% |
| Tween 60 | 2–3% |
| Sodium lauryl sulphate | 1–2% |
| Preservative | 0.1% |
| Water | to 100% |

EXAMPLE 7

| Diethyl succinate | 50% |
|---|---|
| Ethylene glycol monomethyl ether | 10% |
| Glycerin monosterate (self-emulsifying B.P.) | 10% |
| Generol E-5 | 5% |
| Anhydrous lanolin | 5% |
| Hard paraffin | 5% |
| Water | 17% |

EXAMPLE 8

| Diethyl succinate | 50% |
|---|---|
| Ethylene glycol monomethyl ether | 10% |
| Span 60 | 10% |
| Anhydrous lanolin | 3% |
| Hard paraffin | 3% |
| Generol E-10 | 5% |
| Water | 17% |

EXAMPLE 9

| Diethyl succinate | 50% |
|---|---|
| Ethylene glycol monomethyl ether | 10% |
| Glycerin monostearate (self-emulsifying B.P.) | 5% |
| Generol E-5 | 5% |
| Anhydrous lanolin | 5% |
| Water | 25% |

EXAMPLE 10

| Diethyl succinate | 50% |
|---|---|

-continued

| Glycerin monostearate (self-emulsifying B.P.) | 8% |
| --- | --- |
| Generol E-5 | 4% |
| Anhydrous lanolin | 4% |
| Hard paraffin | 4% |
| Water | 30% |

EXAMPLE 11

| Diethyl succinate | 50% |
| --- | --- |
| Span 60 | 8% |
| Generol E-5 | 4% |
| Anhydrous lanolin | 4% |
| Hard paraffin | 4% |
| Water | 30% |

EXAMPLE 12

| Diethyl succinate | 60% |
| --- | --- |
| Glycerin monostearate (self-emulsifying B.P.) | 5% |
| Generol E-5 | 2% |
| Hard paraffin | 2% |
| Anhydrous lanolin | 1% |
| Stearic Acid | 2% |
| Water | 30% |

EXAMPLE 13

| Diethyl succinate | 50% |
| --- | --- |
| Span 60 | 8% |
| Generol E-5 | 4% |
| Wood alcohols | 4% |
| Hard paraffin | 4% |
| Water | 30% |

EXAMPLE 14

| Diethyl succinate | 50% |
| --- | --- |
| Ethylene glycol monomethyl ether | 10% |
| Glycerin monostearate | 5% |
| Generol E-5 | 3% |
| Bees Wax | 4% |
| Hard paraffin | 3% |
| Water | 25% |

EXAMPLE 15

| Diethyl succinate | 50% |
| --- | --- |
| Ethylene glycol monomethyl ether | 10% |
| Span 60 | 11% |
| Emulsifying wax (B.P.) | 5% |
| Hard paraffin | 4% |
| Anhydrous lanolin | 5% |
| Water | 15% |

EXAMPLE 16

| Diethyl succinate | 60% |
| --- | --- |
| Glycerin monostearate | 8% |
| Generol E-5 | 4% |
| Anhydrous lanolin | 5% |

-continued

| Hard paraffin | 3% |
| --- | --- |
| Water | 20% |

I claim:

1. A cosmetic cleansing cream for nail varnish removal and skin cleansing comprising between about 40 and 60 percent by weight of diethyl succinate, between about 3 and 10 percent by weight of a lipid, between about 5 and 29 percent by weight of an emulsifier, and the balance water.

2. The cosmetic cleansing cream of claim 1 wherein the lipid is lanolin, a plant oil, a plant fat, paraffin, cholesterol, or sitosterol.

3. The cosmetic cleansing cream of claim 1 wherein the emulsifier comprises a primary emulsifier of an emulsifying wax, glycerin monostearate, a polyoxyethylene sterol; a secondary emulsifier of sodium lauryl sulfate; or mixtures thereof.

4. The cosmetic cleansing cream of claim 1 further comprising a preservative in an amount of 0.1 to 0.5 percent by weight.

5. The cosmetic cleansing cream of claim 4 wherein the preservative is butylated hydroxy anisole or butylated hydroxy toluene.

6. The cosmetic cleansing cream of claim 1 further comprising a moisturizer in an amount of between 5 and 15 weight percent.

7. The cosmetic cleansing cream of claim 6 wherein the moisturizer is a monomethyl ether of ethylene or propylene glycol.

8. A cosmetic cleansing cream for nail varnish removal and skin cleansing consisting essentially of between about 40 and 60 percent by weight of diethyl succinate, between about 3 and 10 percent by weight of a lipid, between about 5 and 29 percent by weight of an emulsifier, and the balance water.

9. The cosmetic cleansing cream of claim 8 wherein the lipid is lanolin, a plant oil, a plant fat, paraffin, cholesterol, or sitosterol.

10. The cosmetic cleansing cream of claim 8 wherein the emulsifier comprises a primary emulsifier of an emulsifying wax, glycerin monostearate, a polyoxyethylene sterol; a secondary emulsifier of sodium lauryl sulfate; or mixtures thereof.

11. A cosmetic cleansing cream for nail varnish removal and skin cleansing comprising between about 40 and 60 percent by weight of diethyl succinate, between about 3 and 10 percent by weight of a lipid, between about 5 and 29 percent by weight of an emulsifier; a preservative in an amount of 0.1 to 0.5 percent by weight; a moisturizer in an amount of between 5 and 15 weight percent and the balance water.

12. The cosmetic cleansing cream of claim 11 wherein the lipid is lanolin, a plant oil, a plant fat, paraffin, cholesterol, or sitosterol.

13. The cosmetic cleansing cream of claim 11 wherein the emulsifier comprises a primary emulsifier of an emulsifying wax, glycerin monostearate, a polyoxyethylene sterol; a secondary emulsifier of sodium lauryl sulfate; or mixtures thereof.

14. The cosmetic cleansing cream of claim 11 wherein the preservative is butylated hydroxy anisole or butylated hydroxy toluene.

15. The cosmetic cleansing cream of claim 11 wherein the moisturizer is a monomethyl ether of ethylene or propylene glycol.

* * * * *